(12) United States Patent
Maes et al.

(10) Patent No.: US 6,411,933 B1
(45) Date of Patent: Jun. 25, 2002

(54) METHODS AND APPARATUS FOR CORRELATING BIOMETRIC ATTRIBUTES AND BIOMETRIC ATTRIBUTE PRODUCTION FEATURES

(75) Inventors: Stephane Herman Maes, Danbury; Geoffrey G. Zweig, Greenwich, both of CT (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/444,684

(22) Filed: Nov. 22, 1999

(51) Int. Cl.[7] .............................................. G10L 21/00
(52) U.S. Cl. ...................................... 704/273; 704/270
(58) Field of Search ................................ 704/270, 273, 704/275, 231, 246, 251

(56) References Cited

U.S. PATENT DOCUMENTS

| | | | | |
|---|---|---|---|---|
| 5,171,930 A | * | 12/1992 | Teaney | 84/725 |
| 5,719,950 A | * | 2/1998 | Osten et al. | 382/115 |
| 5,729,694 A | | 3/1998 | Holzrichter et al. | 704/208 |
| 5,732,133 A | * | 3/1998 | Mark | 379/355 |
| 5,745,555 A | * | 4/1998 | Mark | 379/95 |
| 5,897,616 A | * | 4/1999 | Kanevsky et al. | 704/246 |
| 5,905,972 A | * | 5/1999 | Huang et al. | 704/268 |
| 5,920,477 A | * | 7/1999 | Hoffberg et al. | 364/188 |
| 6,041,300 A | * | 3/2000 | Ittycheriah et al. | 704/255 |
| 6,052,662 A | * | 4/2000 | Hogden | 704/256 |
| 6,107,935 A | * | 8/2000 | Comerford et al. | 340/835.31 |
| 6,161,090 A | * | 12/2000 | Kanevsky et al. | 704/246 |
| 6,219,639 B1 | * | 4/2001 | Bakis et al. | 704/246 |
| 6,219,640 B1 | * | 5/2001 | Basu et al. | 704/246 |

OTHER PUBLICATIONS

"Use of Low Power EM Radar Sensors for Speech Articulator Measurements," EuroSpeech '97 5th European Conference on Speech Communication and Technology, http://speech.llnl.gov/, 14 pages, Sep. 22, 1997.

"Speech Technology Using New Electromagnetic Sensors; Revolutionary Way to Quantify Speech with Many Applications," SpeechTechnology Website, http://speech.lln-l.gov/, 7 pages, May 12, 1998.

"An Introduction to Laryngograph," Laryngograph Ltd., http://www.laryngograph.com/introduction/introduction.html, 2 pages, 1997.

E. Abberton et al., "Real–Time Speech Pattern Element Displays for Interactive Therapy," www.larynogograph.com, 5 pages.

E. Carlson et al., "Aspects of Voice Quality: Display, Measurement and Therapy," www.laryngograph.com, 5 pages.

* cited by examiner

*Primary Examiner*—Marsha D. Banks-Harold
*Assistant Examiner*—Susan McFadden
(74) *Attorney, Agent, or Firm*—Paul J. Otterstedt; Ryan, Mason & Lewis, LLP

(57) ABSTRACT

A method of validating production of a biometric attribute allegedly associated with a user comprises the following steps. A first signal is generated representing data associated with the biometric attribute allegedly received in association with the user. A second signal is also generated representing data associated with at least one feature detected in association with the production of the biometric attribute allegedly received from the user. Then, the first signal and the second signal are compared to determine a correlation level between the biometric attribute and the production feature, wherein the validation of the production of the biometric attribute depends on the correlation level. Accordingly, the invention serves to provide substantial assurance that the biometric attribute offered by the user has been physically generated by the user.

31 Claims, 6 Drawing Sheets

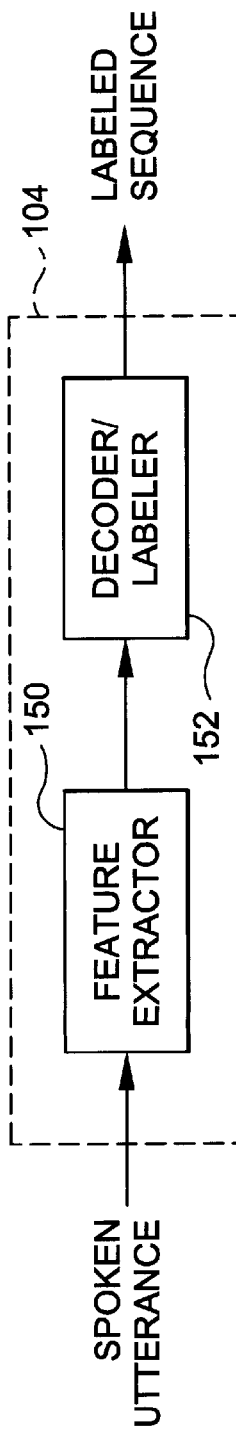
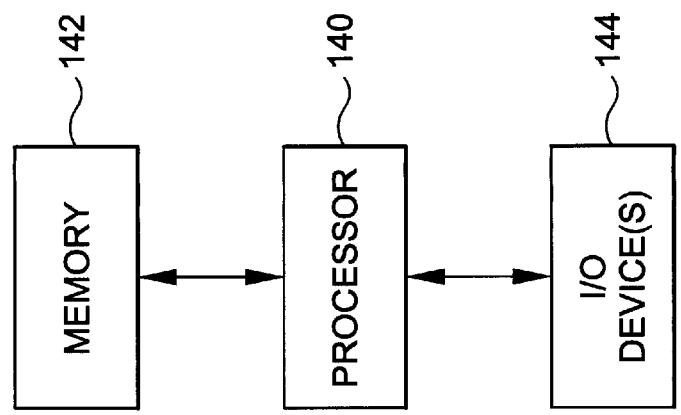
FIG. 2
FIG. 3

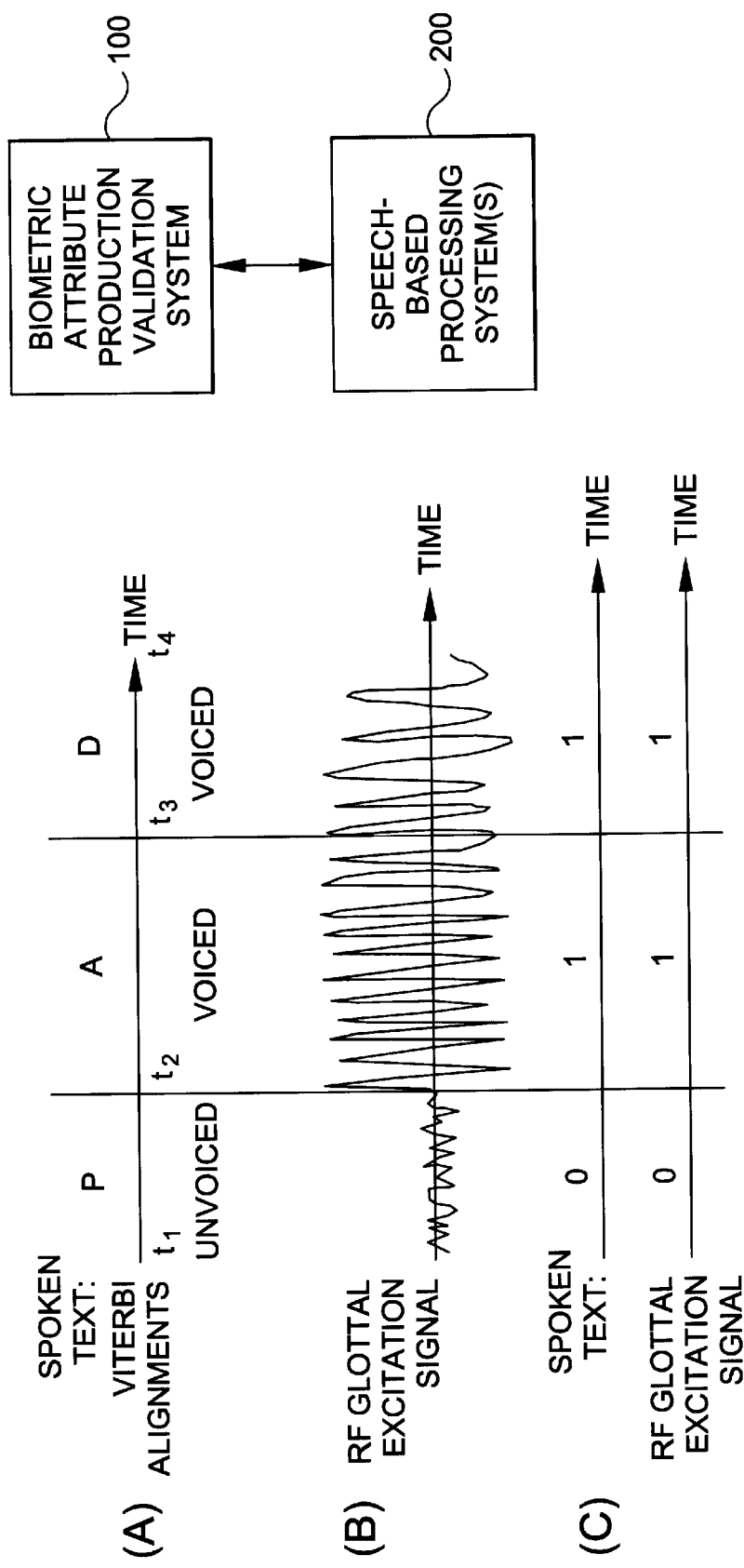

METHODS AND APPARATUS FOR CORRELATING BIOMETRIC ATTRIBUTES AND BIOMETRIC ATTRIBUTE PRODUCTION FEATURES

FIELD OF THE INVENTION

The present invention relates generally to biometric attribute validation and, more particularly, to methods and apparatus for correlating a biometric attribute with one or more biometric attribute production features to validate the production of the biometric attribute.

BACKGROUND OF THE INVENTION

The use of biometric attributes to validate, i.e., identify and/or verify, a person for access to secure applications, systems and/or facilities has increased greatly in the past several years. Some examples of personal biometric attributes that have been used in the validation process include acoustic or speech patterns, fingerprints, retinal scans, to name only a few. Unfortunately, with the increased use of biometric user validation has come increased attempts to deceive the applications, systems and facilities which employ such validation techniques in order to gain unauthorized access. This is especially true in the case of speech biometrics. Some drawbacks of the use of conventional speech biometric techniques in speaker recognition systems for making a validation decision are described below.

When conventional speaker recognition systems are deployed, it is typically assumed that the application manages to verify that the input utterances originate from a live session with a live speaker to enroll, identify or verify. This assumption extends across modalities from text-constrained (e.g., text-dependent, text-prompted, user selected password) to text-independent and speech biometrics. See, for example, U.S. Pat. No. 5,897,616, issued on Apr. 27, 1999, and entitled "Apparatus and Methods for Speaker Verification/Identification/Classification Employing Non-Acoustic and/or Acoustic Models and Databases," the disclosure of which is incorporated by reference herein.

However, with the evolution of digital signal processing (DSP) of digital recordings, as well as advances in text-to-speech (TTS) technology and, in particular, in voice fonts, one can no longer be certain whether a live person is generating the submitted sounds. Voice fonts are known to have the potential to provide the capability to playback or synthesize speech sounding like a given individual based on some training data obtained from the individual and/or voice transformation functions. Compare, for example, U.S. patent application identified by Ser. No. 08/821,520 (docket no. YO996-247), filed on Mar. 21, 1997, and entitled "Speech Synthesis Based on Pre-Enrolled Tokens," the disclosure of which is incorporated by reference herein.

The transition from text-dependent speaker recognition (which is known to be especially vulnerable to recordings) to text-prompted speaker recognition provided somewhat of a solution to the problem. However, even text-prompted speaker recognition does not offer any guarantee against a sophisticated TTS or playback signal processing system. The use of user selected passwords is a proposed extension of the text-prompted speaker recognition concept. However, user selected passwords are easily stolen and used to gain unauthorized access.

Text-independent speaker recognition systems are also essentially defenseless against an efficient TTS/voice font system. Only the use of a conventional text-independent system in the background of a transaction or interaction with a human operator makes it somewhat difficult for a speaker to maintain the flow of the transaction if he uses a TTS/playback system to attempt to fool the recognition system. However, with more sophisticated DSP/TTS capabilities (especially on personal digital assistant or PDA devices), there are no more guarantees with respect to user validation.

The concept of speech biometrics adds a knowledge-based dimension to the recognition process. As is known, see U.S. Pat. No. 5,897,616 and S. Maes, "Conversational Computing," IBM Pervasive Computing Conference, Yorktown Heights, N.Y., June 1999, speech biometric systems use simultaneous content-based recognition (e.g., answers to random questions) and acoustic-based recognition techniques. However, provided that an imposter has the knowledge, a system using speech biometric techniques is essentially defenseless against such an imposter also using sophisticated voice font capabilities. As long as the imposter is able to follow the flow of the dialog, he will likely be able to gain unauthorized access. However, in the case where the speech biometrics system changes multiple non-trivial questions from one access request to another, it is no easy task for an imposter to possess sufficient knowledge and follow the flow of the dialog in order to gain unauthorized access.

Some attempts have been made at detecting the non-linearities of DSP/coders and loudspeakers to detect usage of such devices attempting to fool the system into believing that the person is actually speaking. However, these techniques are not always reliable when dealing with high quality audio equipment or new and unknown equipment.

The use of synchronized biometrics, e.g., face recognition, local mouth geometry recognition, and lip reading synchronized with utterance recognition and speaker recognition has been proposed to guarantee that the user does not use a speaker close to his mouth and lips to generate the utterance. See, for example, U.S. patent application identified by Ser. No. 09/067,829 (docket no. YO997-251), filed on Apr. 28, 1998, and entitled "Method and Apparatus for Recognizing Identity of Individuals Employing Synchronized Biometrics," the disclosure of which is incorporated by reference herein; as well as the above-incorporated U.S. Pat. No. 5,897,616. Although this adds an additional level of security, it may not be completely fool proof against an effective voice font system combined with good lip sync capabilities.

Accordingly, it is clear that a need exists for techniques that can better guarantee that a speaker physically produced a subject utterance. More generally, a need exists for techniques that can better guarantee that a given biometric attribute has been physically produced by the person offering the biometric attribute as his own.

SUMMARY OF THE INVENTION

The present invention provides methods and apparatus for validating the production of a biometric attribute that better guarantee that a given biometric attribute has been physically produced by the person offering the biometric attribute as his own.

In one broad aspect of the invention, a method of validating production of a biometric attribute allegedly associated with a user comprises the following steps. A first signal is generated representing data associated with the biometric attribute allegedly received in association with the user. A second signal is also generated representing data associated with at least one feature detected in association with the production of the biometric attribute allegedly received from the user. Then, the first signal and the second signal are compared to determine a temporal correlation level between the biometric attribute and the production feature, wherein the validation of the production of the biometric attribute depends on the correlation level. Accordingly, the invention serves to provide substantial assurance that the biometric attribute offered by the user has been physically generated by the user.

In one embodiment, the biometric attribute is a spoken utterance and the production feature is a physiological effect attributable to the production of the spoken utterance alleged to have been produced by the user, e.g., glottal excitation or vibration. The spoken utterance may be decoded and labeled by a speech recognition system to produce the first signal. For example, a sequence of voiced and unvoiced phones is generated from the spoken utterance. Then, a first data value (e.g., a logic value "1") is assigned to a voiced phone and a second data value (e.g., a logic value "0") is assigned to an unvoiced phone. Thus, the first signal represents a sequence of such logic values representing the occurrence of voiced and unvoiced phones from the spoken utterance. In an alternative embodiment, a speaker recognition system may be employed to decode and label the spoken utterance.

The physiological effect attributable to the production of the spoken utterance alleged to have been produced by the user, e.g., glottal excitation or vibration, may be detected by a speech production detecting system, e.g., a laryngograph device or a radar device. The physiological effect may be represented by a time varying signal. Then, to generate the second signal, the time varying signal may be processed to generate a sequence of data values (logic "1"s and "0"s) representing some characteristic of the signal content. For example, since it is known that a relatively lower level of glottal excitation energy is generally associated with unvoiced speech, while a relatively higher level of glottal excitation energy is generally associated with voiced speech, a mean-square value of the excitation signal may be computed for each time period corresponding to a time period associated with the acoustic sequence, and if the mean-square value exceeds a predetermined relative threshold value, a logic "1" may be assigned to that time period, and a logic "0" otherwise. The "relative threshold value" may represent a fixed fraction of the average mean-square value of the entire signal, as will be explained below. Thus, through the use of a relative threshold value, gain/loss effects are advantageously accounted for over each time period.

Thus, in such an embodiment, the comparing operation may comprise a time-aligned comparison of the respective sequences associated with the first signal and the second signal to determine a percentage or relative fraction of matches between the data values representing voiced and unvoiced phones and the data values representing the energy level of the glottal excitation signal over all time periods being considered. The percentages of matches represents the level of correlation. The level of correlation may then be compared to a threshold value. If the level is not less than the threshold value, for example, the production of the biometric attribute is considered validated. That is, the invention provides a substantial assurance that the speech production detecting system is witnessing the actual source of the biometric.

It is to be understood that the speech-based embodiment described above, that is, comparison between the voicing in the acoustic signal and high-energy in the production signal, is not the only manner of determining a correlation level between a spoken utterance and a speech production feature. In one alternative embodiment, the mutual information between the two signals may be used, e.g., see T. M. Cover and J. A. Thomas, "Elements of Information Theory," 1991. In another embodiment, a two-dimensional contingency table may be used in conjunction with a Chi-Square test to measure the association between the two signals, e.g., see E.S. Keeping, "Introduction to Statistical Inference," 1962. In general, any statistical measure of correlation or association may be used. In yet another implementation, the pitch/fundamental from the speech waveform and the glottal excitation signal may be directly extracted (e.g., by the speech or speaker recognition/acoustic system and the speech production/non-acoustic system, respectively) and their periodicities compared.

In yet other approaches, the characteristics to be compared may be the voiced/unvoiced distribution extracted from each signal, or the voiced/unvoiced distribution extracted from the production signal with respect to the energy in the fundamental excitation component of the acoustic signal (e.g., measured by an LPC model as described in S. Furui, "Digital speech processing, synthesis and recognition," Marcel Dekker, New York, N.Y. 1989). When the voiced/unvoiced distribution from the production signal is employed, for example, the glottal energy contained in the production signal may be directly measured in order to extract the voiced/unvoiced decision.

Accordingly, it is to be appreciated that a key to the outcome of the correlation operation is the degree of temporal coincidence between the signal representing the biometric attribute (the first signal) and the signal representing the biometric attribute production feature (the second signal). The comparison is accomplished by extracting the temporal correlation between characteristics associated with both signals. However, any suitable correlation measure/estimator can be used. Given the inventive teachings herein, one of ordinary skill in the art will realize other implementations that are within the scope of the invention.

It is also to be appreciated that the inventive methodology of validating production of a spoken utterance allegedly associated with a user may be employed in conjunction with a speech biometric recognition system. For example, a speaker recognition system may employ the speech biometric techniques described in the above incorporated U.S. Pat. No. 5,897,616. These speech biometric results may be used in conjunction with the results obtained via the above-mentioned spoken utterance production validating methodology to provide an overall validation result with regard to the potential user. It is to also be understood that the invention may be used not only for verification, but also for identification. That is, the invention may determine who is speaking out of a set of pre-enrolled users.

It is further to be appreciated that while the above embodiment describes speech as the biometric, the invention is not so limited. That is, the methods and apparatus of the invention are applicable for use in accordance with other biometrics, e.g., fingerprints, retinal scans, to name only a few. Also, a system according to the invention may be configured to validate the production of more than one biometric attribute at a time.

These and other objects, features and advantages of the present invention will become apparent from the following detailed description of illustrative embodiments thereof, which is to be read in connection with the accompanying drawings.

BRIEF DESCRIPTION OF THE DRAWINGS

FIG. 2 is a block diagram of an exemplary hardware architecture for use in accordance with one or more of the elements of the system of the present invention;

FIG. 3 is a block diagram of an exemplary speech recognition system for use in accordance with one embodiment of the present invention;

FIGS. 7A through 7C are timing diagrams illustrating correlation between a signal representing a spoken utterance and a signal representing the production of a spoken utterance; and FIG. 8 is a block diagram illustrating integration of a biometric attribute production validation system according to the invention with one or more speech-based processing systems.

DETAILED DESCRIPTION OF PREFERRED EMBODIMENTS

The present invention will be explained below in the context of an illustrative speech-based implementation. However, it is to be understood that the present invention is not limited to such a particular biometric. Rather, the invention is more generally applicable to any situation in which it is desirable to validate the production or generation of one or more biometric attributes offered by a user as his own. As will be explained, the result of the validation may be used alone or in conjunction with other validating processes to validate a potential user. The potential user may be seeking access to secure applications, systems and/or facilities. It is to also be understood that the invention may be used not only for verification, but also for identification. That is, the system may determine who is speaking out of a set of pre-enrolled users.

Figure 1:
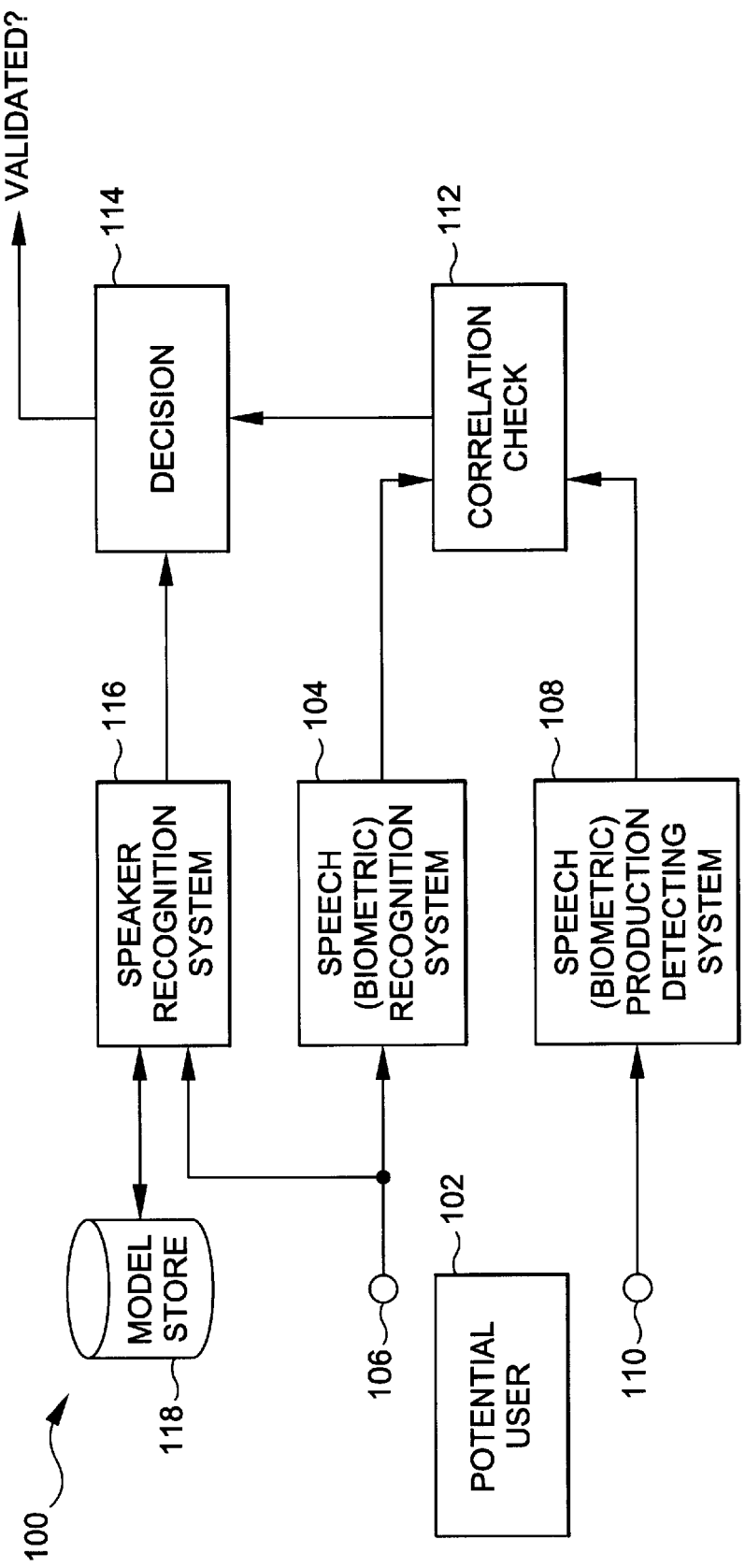
FIG. 1 is a block diagram of a system for validating the production of a biometric attribute according to one embodiment of the present invention.

Referring to FIG. 1, is a block diagram of a system for validating the production of a biometric attribute according to one embodiment of the present invention. The system 100 is responsive to a potential user 102 (e.g., a user seeking access to some application, system and/or facility, not shown) and includes: a speech recognition system 104 with an audio capturing device 106 (e.g., a microphone); a speech production detecting system 108 with a speech production capturing device 110 (e.g., an electromagnetic wave-based sensor, a laryngograph sensor); a correlation check module 112, a decision module 114, a speaker recognition system 116, and a model store 118.

It is to be appreciated that the speech recognition system 104 may be implemented using known speech recognition systems and techniques. Preferably, the speech recognition system decodes and labels the spoken utterance to generate a time-aligned (e.g., Viterbi aligned) transcription or time-aligned labels. An example of such a labeling system is disclosed in U.S. patent application identified by Ser. No. 09/015,150 (docket no. YO997-386) and entitled "Apparatus and Method for Generating Phonetic Transcription from Enrollment Utterances," the disclosure of which is incorporated by reference herein. As will be explained below, the speech recognition system 104 generates a time-aligned sequence of voiced and unvoiced phones from the spoken utterance, whereby one logic value is assigned to voiced phones and another to unvoiced phones. The microphone 106 captures the spoken utterances to be processed by the speech recognition system 104 and the speaker recognition system 116.

The speech production detecting system 108 may be implemented using known speech production detection systems and techniques. The speech production detecting system detects one or more features associated with the production of a spoken utterance. In one embodiment, the detecting system 108 may be a laryngograph device. As is known, a laryngograph device utilizes electro-laryngography (also known as electro-glottography, EGG) techniques to monitor vocal fold contact without interfering in the normal process of speaking. Examples of laryngograph devices and techniques that may be employed by the speech production detecting system 108 of the invention are described at the website www.laryngograph.com. Conventional electro-laryngography techniques typically require direct contact between the person to be tested and the sensor 110 of the laryngograph device.

In an alternative embodiment, an electromagnetic wave-based (e.g., radar) system may be used as the speech production detecting system 108. One advantage of using a radar based system is that the user and device sensor 110 do not need to be in direct physical contact. Another advantage is that such a system may detect physiological effects associated with speech at different locations of the speaker, e.g., lip area, chin area, throat area. There are several such systems known in the art which may be employed. For example, a radar system such as described in U.S. Pat. No. 5,729,694 ('694 system), the disclosure of which is incorporated herein by reference, may be employed as the speech production detecting system 108. Such an electromagnetic wave-based device is also discussed at the website speech.llnl.gov. In one preferred embodiment, a portion of the '694 system (e.g., the detecting equipment located at the throat area) may be employed. This will be explained in the context of FIG. 6 below.

Regardless of the type of system and technique employed, the speech production detecting system 108 preferably generates a time varying signal (e.g., a signal that varies in energy level over time) that represents a physiological effect associated with a spoken utterance. This physiological effect may be glottal excitation or vibration. Then, the speech production detecting system preferably generates a sequence of logic values representing some characteristic of the time varying signal content. For example, since it is known that a lower level of glottal excitation energy is generally associated with unvoiced speech, while a higher level of glottal excitation energy is generally associated with voiced speech, a mean-square value of the excitation signal is computed for each time period corresponding to a time period associated with the acoustic sequence (generated by the speech recognition system 104). If the mean-square value exceeds a predetermined relative threshold value, a logic "1" is assigned to that time period, and a logic "0" otherwise. The "relative threshold value" may represent a fixed fraction of the average mean-square value of the entire signal. For instance, a group of contiguous time periods that results in a sequence of mean-square values of 1, 100, 99, 100, 2, 100, and 100, will result in the same sequence of logic values (1's and 0's) as a group of contiguous time periods that result in a sequence of mean-square values of 100, 10000, 9900, 10000, 200, 10000, 10000, when a relative threshold of 0.5 times the average is used. In such example, both sequences of mean-square values result in a logic value sequence of 0111011. As is to be appreciated with respect to this example, the second sequence of mean-square values is merely a scaled-up (by 100) version of the first sequence of mean-square values. Thus, through the use of a relative threshold value, gain/loss effects are advantageously accounted for over each time period.

The speaker recognition system 116 may be implemented using conventional speaker recognition systems and techniques. For example, a speaker recognition system which may be employed is described in U.S. patent application identified by Ser. No. 08/788,471 (docket no. YO996-188), filed on Jan. 28, 1997, and entitled "Text Independent Speaker Recognition for Transparent Command Ambiguity Resolution and Continuous Access Control," the disclosure of which is incorporated by reference herein. As is known, the system 116 may use models stored in model store 118 to perform the recognition function. Potential system users may enroll prior to use. The speaker recognition system may be used to separately validate the potential user 102 in combination with the production validation procedure of the invention. Alternatively, if a speaker recognition system includes utterance decoding and labeling capabilities, the system 116 may completely replace the speech recognition system 104. That is, the system 116 may generate the time-aligned phone sequence for use in the correlation check module.

As will be illustratively explained, the respective signals output by the speech recognition system 104 and the speech production detecting system 108 are compared in the correlation check module 112. The result of the correlation check is then provided to the decision module 114. The module 114 takes the speech production feature validation result from the correlation check module 112 and the speaker recognition result from the speaker recognition system and makes an overall validation decision.

Referring to FIG. 2, a block diagram is shown of an exemplary hardware architecture for implementing one, more or all of the elements of the system 100 shown in FIG. 1. In this embodiment, the system 100 may be implemented by a processor 140, memory 142, and I/O devices 144. It is to be appreciated that the term "processor" as used herein is intended to include any processing device, such as, for example, one that includes a CPU (central processing unit). For example, the processor may be a digital signal processor, as is known in the art. Also the term "processor" may refer to one or more individual processors. The term "memory" as used herein is intended to include memory associated with a processor or CPU, such as, for example, RAM, ROM, a fixed memory device (e.g., hard drive), a removable memory device (e.g., diskette), flash memory, etc. In addition, the term "input/output devices" or "I/O devices" as used herein is intended to generally include, for example, one or more input devices, e.g., microphone, sensor, etc., for inputting data and other signals to the processing unit, and/or one or more output devices, e.g., display, speaker, etc., for providing results associated with the processing unit. For example, the display or speaker may provide a potential user with the access decision reached by the system. Accordingly, computer software including instructions or code for performing the methodologies of the invention, as described herein, may be stored in one or more of the associated memory devices (e.g., ROM, fixed or removable memory) and, when ready to be utilized, loaded in part or in whole (e.g., into RAM) and executed by a CPU. In any case, it should be understood that the elements illustrated in the figures may be implemented in various forms of hardware, software, or combinations thereof, e.g., one or more digital signal processors with associated memory, application specific integrated circuit(s), functional circuitry, one or more appropriately programmed general purpose digital computers with associated memory, etc. Given the teachings of the invention provided herein, one of ordinary skill in the related art will be able to contemplate other implementations of the elements of the invention.

Referring now to FIG. 3, a block diagram of an exemplary speech recognition system 104 for use in accordance with one embodiment of the present invention is shown. As shown, the speech recognition system includes a feature extractor 150 and a speech decoder/labeler 152. As is well known in the art, the feature extractor receives the spoken utterance captured by the microphone 106 and extracts feature vector signals therefrom. The type of feature vector employed is not critical to the invention. The decoder/labeler 152 then produces a sequence of voiced and unvoiced phones from the feature vectors. This may be done by time-aligning pre-stored phones with the feature vectors representing the input audio signal. Thus, a sequence of phones is generated having time boundaries. Then, a first data value (e.g., a logic value "1") is assigned to a voiced phone and a second data value (e.g., a logic value "0") is assigned to an unvoiced phone. Thus, the speech recognition system produces a signal which represents a sequence of such logic values representing the occurrence of voiced and unvoiced phones from the spoken utterance.

Figure 4:
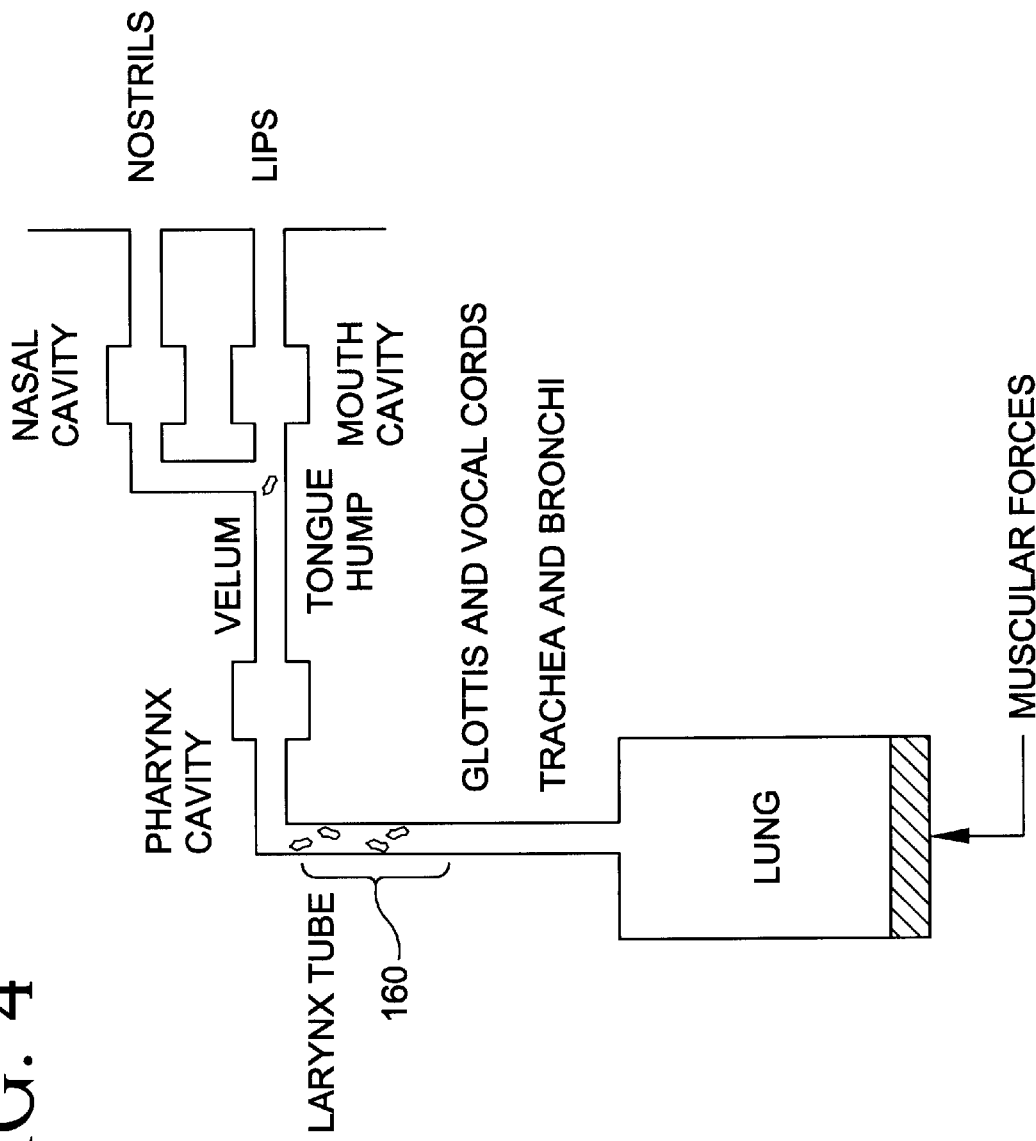
FIG. 4 is diagram illustrating a speech production model.
Figure 5:
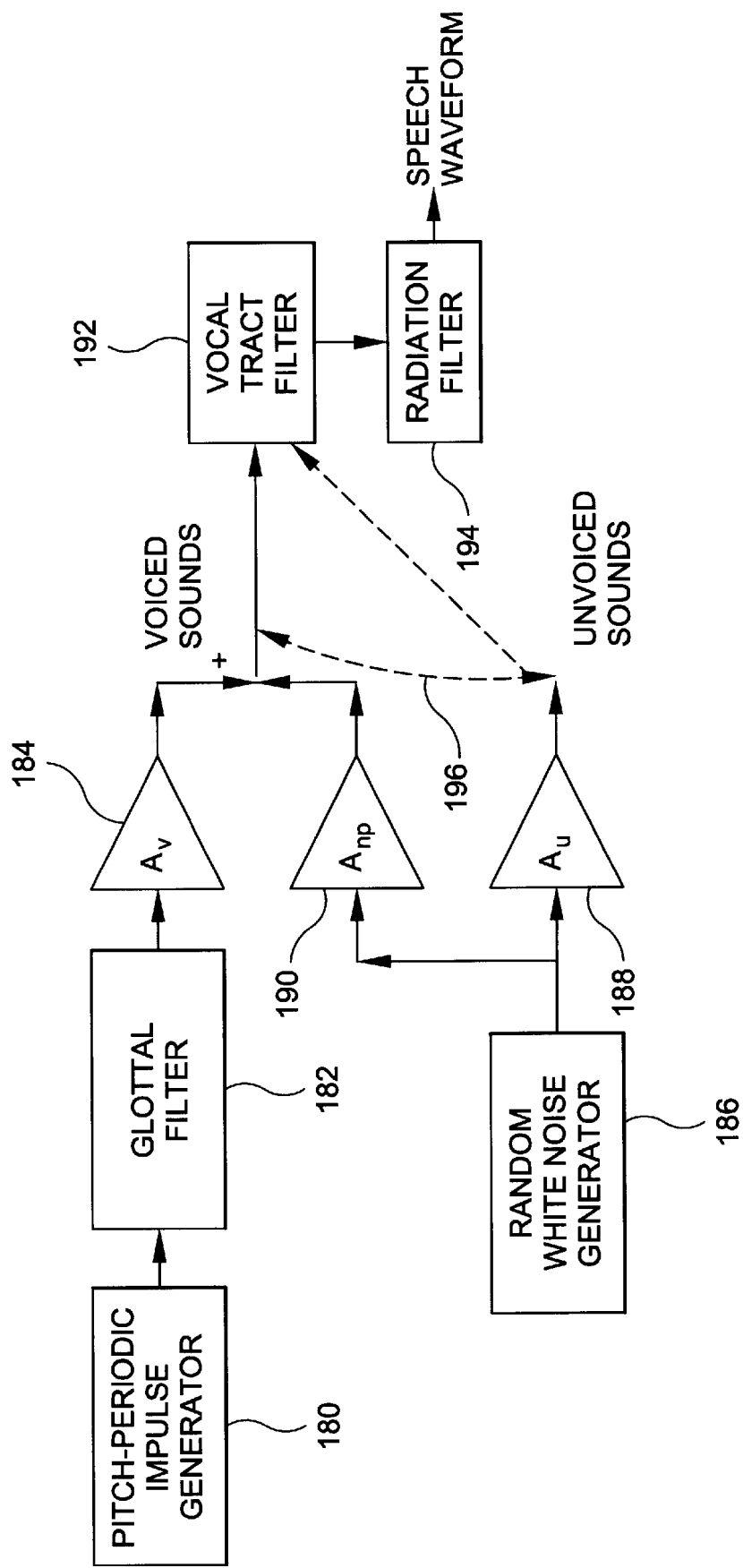
FIG. 5 is diagram illustrating a source filter model for speech production.

Referring now to FIGS. 4 and 5, respective diagrams illustrating a speech production model and a source filter model for speech production are shown. Vocal system models are generally described by an excitation source which drives an acoustic resonator tract, from whence the sound pressure wave radiates to a listener or to a microphone. There are two major types of speech: (1) "voiced" where the vocal folds open and close rapidly, at approximately 70 to 200 Hz, providing periodic bursts of air into the vocal tract; and (2) "unvoiced" excitations where constrictions in the vocal tract cause air turbulence and associated modified-white acoustic-noise. A few sounds are made by both processes at the same time.

The human vocal tract is a complex acoustic-mechanical filter that transforms the excitation (i.e., noise source or air pressure pulses) into recognizable sounds, through mostly linear processes. Physically, the human vocal tract can be modeled by a series of tubes of different lengths, different area shapes, with side branch resonator structures, nasal passage connections, and both mid and end point constrictions. As the excitation pressure wave proceeds from the excitation source to the mouth (and/or nose), it is constantly being transmitted and reflected by changes in the tract structure, and the output wave that reaches the lips (and nose) is strongly modified by the filtering processes. In addition, the pressure pulses cause the surrounding tissue to vibrate at low levels which affects the sound as well. It is also known that a backward propagating wave (i.e., reflecting wave off of vocal tract transitions) does travel backward toward the vocal folds and the lungs. It is not heard acoustically, but it can influence the glottal system and it does cause vocal tract tissue to vibrate.

Such vibrations can be measured in accordance with the sensor 110 of the speech production detecting system 108. As shown in FIG. 4, the vibrations that are detected by the sensor 110 are approximately produced in the area denoted as 160. That is, the glottis and the surrounding area is the source of the physiological effect that is preferably detected by the system 108 and represented in the signal to be correlated with the signal generated by the speech recognition system 104.

FIG. 5 illustrates the source filter model for speech production. For voiced sounds, a pitch-periodic impulse generator 180 produces a signal that is filtered by a filter 182 representing the glottis and amplified by amplifier 184. Random white noise from generator 186 is amplified by amplifier 190 and mixed with the output of amplifier 184 to generate voiced sounds. For unvoiced sounds, random white noise is amplified by amplifier 188. Voiced sounds and unvoiced sounds are then passed through filters 192 and 194 which respectively represent the vocal tract and sound radiation effects. The output of the radiation filter 194 represents a speech waveforn or spoken utterance. Dashed line 196 represents the fact that the input to the vocal tract filter may be switched between voiced or unvoiced sounds.

Figure 6:
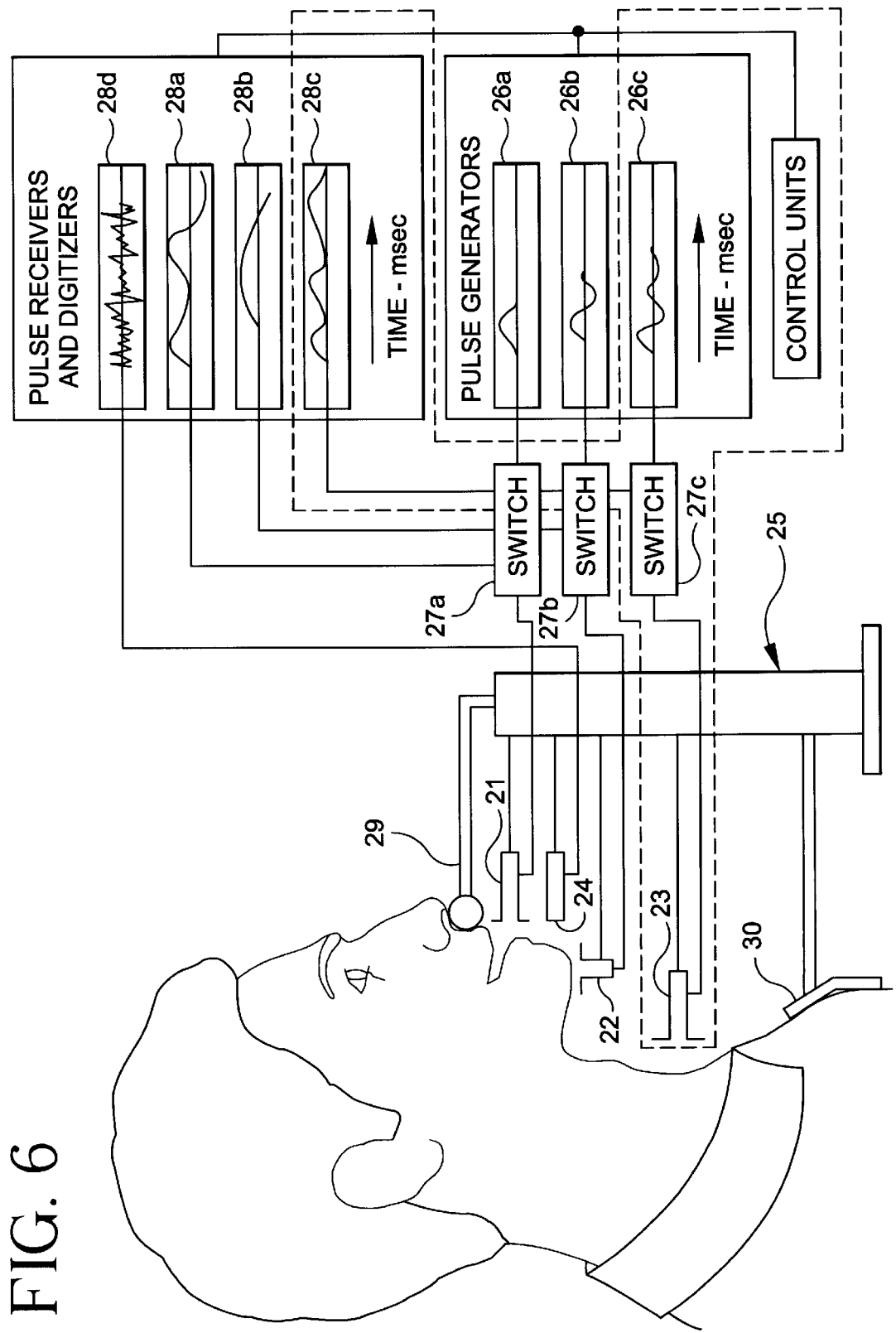
FIG. 6 is a block diagram of an exemplary speech production detecting system for use in accordance with one embodiment of the present invention.

Referring now to FIG. 6, a block diagram of a portion of an exemplary speech production detecting system for use in accordance with one embodiment of the present invention is shown. The embodiment shown in FIG. 6 is taken from the above-incorporated '694 patent. FIG. 6 shows apparatus according to the '694 patent for measuring the simultaneous properties of several speech organs using electromagnetic wave-based sensors. A view of a head with three antennas 21, 22, 23 and an acoustic microphone 24 mounted on a support stand 25 is shown. Antennas 21, 22, 23 are connected to pulse generators 26a, b, c through transmit/receiver switches 27a, b, c respectively. Pulse generators 26a, b, c apply pulses to antennas 21, 22, 23, which are directed to various parts of the vocal system. Antennas 21, 22, 23 pick up reflected pulses, which are then transmitted back through switches 27a, b, c to pulse receivers and digitizers (e.g., sample and hold units) 28a, b, c. Support stand 25 positions the antennas 21, 22, 23 to detect signals from various parts of the vocal tract, e.g., by using face positioning structure 29 and chest positioning structure 30. As shown, antenna 21 is positioned to detect the tongue, lip, velum, etc. Antenna 22 is positioned to detect tongue and jaw motion and antenna 23 is position to detect vocal fold motion or glottal excitation.

While one or more portions of the apparatus shown in FIG. 6 may be employed in accordance with the invention, in a preferred embodiment, only one of the antennas or sensors and its associated equipment is used. Antenna 23, pulse generator 26a, switch 27c, pulse receiver 28b, and the control units are preferably used to detect and measure the glottal vibrations produces when the potential user speaks. These elements are collectively denoted by reference letter A. It is to be appreciated that the antenna 23 corresponds to the speech production feature capturing sensor 110 of FIG. 1. Thus, in response to the glottal vibration measured by the antenna 23, the pulse receivers and digitizer 28b produces the time varying signal that is then further processed to generate the sequence of logic values used in the correlation check module 112 of FIG. 1, as will be further explained below.

Accordingly, with reference to FIGS. 1 and 7A through 7C, a potential user 102 allegedly utters a speech sample in the presence of the system 100. The spoken utterance is alleged to have been physically produced by the user, since there is the possibility that the user is lip synching to a played back recording or DSP reproduced utterance previously spoken by an authorized user. The microphone 106 captures the audio signal and provides it to the speech recognition system 104 and the speaker recognition system 116. The speech recognition system 104 generates the time-aligned sequence of voiced and unvoiced phones representing the spoken utterance, as previously explained. This sequence is shown in FIG. 7A. As explained, this sequence may be replaced with a corresponding sequence of logic ones and zeros, e.g., "1" for a voiced phone and "0" for an unvoiced phone. The speech recognition system may be a speech recognition engine, a ballistic labeler, a phone classifier, or simply a voice/unvoiced detector. A full speech recognition system is especially useful when the present invention is embedded in a speech biometric system such as described in the above-incorporated U.S. Pat. No. 5,897, 616.

Contemporaneously, the speech production detecting system 108 detects and measures the actual glottal excitation produced by the user at the time the spoken utterance is offered. The system 108 produces the time varying signal representing this physiological effect. The glottal excitation signal is shown in FIG. 7B. Further, the system 108 processes the glottal excitation signal to generate a binary sequence, similar to the binary sequence generated by the speech recognition system 104. In one embodiment, the system 108 divides the glottal excitation signal into time periods, e.g., 10 milliseconds. Preferably, the time period corresponds to the same time period associated with the sequence generated by the system 104. Thus, during the correlation operation as will be explained, the signals may be more easily time-aligned. It is to be appreciated that the glottal excitation signal from the production system may have to be time-delayed by a small constant amount to bring it into correspondence with the audio signal. The amount of time is the amount of time it takes a sound wave to travel from the glottis to the microphone. This can be measured in advance, or determined by finding the single delay that brings the two signals into the best correspondence.

Next, a mean-square value for each time period of the glottal excitation signal and an average mean-square value for the entire glottal excitation signal are computed. This may be done in a conventional manner. If the mean-square value exceeds a predetermined relative threshold value, in this case, a fixed fraction of the average mean-square value of the entire glottal excitation signal, a logic "1" is assigned to that time period. If not, then a logic "0" is assigned. The idea behind the use of a relative threshold value, e.g., a fixed fraction of the average mean-square value of the entire glottal excitation signal, was explained above. In an alternative implementation, the glottal energy may be compared with the average energy in several surrounding time frames, rather than over the whole signal. In either way, a sequence of logic values is generated which represents a characteristic of the signal detected by the sensor 110 of the system 108. In this case, it is the relative energy level of the glottal excitation signal over the time period. That is, since the energy level of the glottal excitation signal may fluctuate, computing a mean-square value and comparing it to an average mean-square value of the entire signal serves to determine a more reliable measure. Thus, the binary sequence generated by the system 108 represents which time periods the glottal excitation is above a certain relative energy threshold and which time periods it is below the relative threshold.

The binary sequence from the speech recognition system 104 and the binary sequence from the speech production detecting system 108 are provided to module 112 which compares how closely the two signals correlate. As is known, a relatively high mean-square value for the energy level of a glottal excitation signal is known to be associated with voiced sound and a relatively low mean-square value for the energy level of a glottal excitation signal is known to be associated with unvoiced sound. Thus, if the person offering the spoken utterance as his own actually produced the utterance, then there should be a substantial match between the voiced/unvoiced phones and the relative higher/ lower energy level of the glottal excitation, respectively. More simply, because the extracted signals are converted to binary signals, there should be a substantial match between the occurrence of logic "1"s and logic "0"s of the sequences. The percentage or relative fraction of matches represents the level of correlation. The level of correlation is then compared to a threshold value in module 112. Preferably, if the level is not less than the threshold value, for example, the module 112 indicates that the production of the spoken utterance is validated. That is, the module 112 provides a substantial assurance that the speech production detecting system 108 actually witnessed the actual source of the spoken utterance.

In an alternative embodiment, the correlation module 112 may receive the time varying glottal excitation signal directly from the system 108 and, itself, generate the binary sequence based on the computation of mean-square values of the energy level.

In FIGS. 7A through 7C, an example of the correlation process is shown over three discrete time periods. As shown in FIG. 7A, the speech recognition system 108 determined that the spoken utterance included an unvoiced sound between time t1 and t2, and respective voiced sounds between times t2 and t3 and between times t3 and t4. As shown in FIG. 7B, the speech production detecting system 108 determined that the glottal excitation signal had a relative low energy level between times t1 and t2, and respective relative high energy levels between times t2 and t3 and between times t3 and t4. FIG. 7C illustrates the corresponding time-aligned binary sequences for the spoken utterance and the glottal excitation signal. Advantageously, once the corresponding two binary sequences are time-aligned, it can be seen whether an appropriate glottal energy level occurred when a particular phone was supposed to have been spoken. As shown, lower frequency energy occurred when an unvoiced sound was received (sound "P" in time segment t1 to t2), and higher frequency energy occurred when voiced sounds were received (sounds "A" in time segment t2 to t3 and "D" in time segment t3 to t4). Thus, in this example, 100% correlation is determined. However, this is not necessarily required. That is, the percentage of time segment matches may only have to be at or above a certain threshold value for the module 112 to indicate validation. If the correlation level is below the threshold, it is determined that the person offering the spoken utterance likely did not actually produce it in the presence of the system. Thus, the production is not validated. Accordingly, it is to be appreciated that a key to the outcome of the correlation operation performed by module 112 is the degree of temporal coincidence between the sequences. It is to be appreciated that the above-described process for determining temporal correlation is but one example of a correlation/estimation technique that may be employed. Thus, other correlators/estimators can be employed by the invention.

The correlation check module 112 can then send its result to the decision module 114. If the speech feature production is validated and the speaker is also validated by the system 116, the potential user 102 is considered to be completely validated. The system 100 then informs the application, system and/or facility (not shown) that the user is validated and thus authorized for access.

It is to be understood that the speaker recognition system 116 preferably performs speech biometric recognition on the acoustic signal received at the microphone 106. The speaker recognition system 116 may, for example, employ the speech biometric techniques described in the above-incorporated U.S. Pat. No. 5,897,616. These result may be used in the decision block 114 in conjunction with the results obtained by the correlator 112 to provide an overall validation result with regard to the potential user.

It is to be understood that the speech-based embodiment described above is not the only manner of determining a correlation level between a spoken utterance and a speech production feature. In one alternative embodiment, previously mentioned, the mutual information between the two signals may be used. In another embodiment, previously mentioned, a two-dimensional contingency table may be used in conjunction with a Chi-Square test to measure the association between the two signals. In general, any statistical measure of correlation or association may be used. In yet another implementation, the pitch/fundamental from the speech waveform and the glottal excitation signal may be directly extracted (e.g., by the speech or speaker recognition/ acoustic system and the speech production/non-acoustic system, respectively) and their periodicities compared. Given the inventive teachings herein, one of ordinary skill in the art will realize other implementations that are within the scope of the invention.

It is to be appreciated that the system 100 of the invention may be combined with one or more speech-based processing systems such as, for example, text-dependent, text-prompted, user selected password, text-independent, speech biometrics, and synchronized biometric systems. Certain of these speech-based processing systems may be integrated internal to the recognition systems 104 and 116 (e.g., as mentioned above, speech biometrics may be performed by the speaker recognition system 116) or the inventive system may be integrated with one or more of these speech-based processing systems. Examples of these systems are respectively described in the above-incorporated U.S. patent application identified by Ser. No. 08/788,471 (docket no. YO996-188); the above-incorporated U.S. Pat. No. 5,897,616; and the above-incorporated U.S. patent application identified by Ser. No. 09/067,829 (docket no. YO997-251). FIG. 8 is a block diagram illustrating integration of a biometric attribute production validation system 100 (FIG. 1) according to the invention with one or more of these speech-based processing systems.

Speech production detection and utterance synchronization techniques of the invention provide an improved way to substantially guarantee that the speaker indeed physically produced the utterance. It serves to guard against play back, voice fonts and other schemes to attempt to fool audio-based recognition systems.

As mentioned, the invention is applicable to biometric attributes other than speech. For instance, in the case of fingerprints, attempts have been made to validate their production by measuring the temperature of the finger or detecting a pulse on a finger. However, these conventional approaches can be circumvented by placing an artificially lifted fingerprint on a heated and pulsing plastic finger. The invention can solve this problem by using radar measurements to detect movement of the subject, e.g., arm, hand and/or finger movement, and verify that the movement is consistent with a living person. Internal body structures and motions, e.g., bone and muscle movements, pulsating arteries, and/or bone structure, can also be checked for consistency. Since the invention provides methods for verifying the source of biometric signals, it may also be applied in the classical retina scan and infrared face temperature measuring system to provide assurance that the measurement is being done on a live individual. Also, by way of example, temperature of an object and patterns of blood vessels measured via infrared sensing techniques may be used. In accordance with yet another exemplary embodiment, handwriting verification and sonar or ultrasound measurements may be employed in accordance with the invention.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method of validating production of a biometric attribute allegedly associated with a user, the method comprising the steps of:
   generating a first signal representing data associated with the biometric attribute allegedly received in association with the user;
   generating a second signal representing data associated with at least one feature detected in association with the production of the biometric attribute allegedly received from the user; and
   comparing the first signal and the second signal to determine a correlation level between the biometric attribute and the production feature, wherein validation of the production of the biometric attribute depends on the correlation level.

2. The method of claim 1, further comprising the step of validating the production of the biometric attribute when the correlation level is not less than a threshold value.

3. The method of claim 1, wherein the biometric attribute is a spoken utterance alleged to have been produced by the user.

4. The method of claim 3, wherein the production feature is a physiological effect attributable to the production of the spoken utterance alleged to have been produced by the user.

5. The method of claim 4, wherein the first signal is generated by an audio-based recognition system.

6. The method of claim 5, wherein the audio-based recognition system is a speech recognition system.

7. The method of claim 5, wherein the audio-based recognition system is a speaker recognition system.

8. The method of claim 4, wherein the second signal is generated by a speech production detecting system.

9. The method of claim 8, wherein the speech production detecting system is in physical contact with the user.

10. The method of claim 9, wherein speech production detecting system is a laryngograph device.

11. The method of claim 8, wherein the speech production detecting system is not in physical contact with the user.

12. The method of claim 11, wherein speech production detecting system is an electromagnetic wave-based detecting device.

13. The method of claim 12, wherein the electromagnetic wave-based detecting device is a radar-based device.

14. The method of claim 5, wherein the audio-based recognition system produces a sequence of time-aligned phones associated with the spoken utterance.

15. The method of claim 5, wherein the audio-based recognition system assigns a first data value to a voiced phone and a second data value to an unvoiced phone such that the first signal represents a time-aligned sequence of first and second data values.

16. The method of claim 8, wherein the speech production detecting system detects a time varying signal representing the physiological effect attributable to the production of the spoken utterance alleged to have been produced by the user.

17. The method of claim 16, wherein the physiological effect is a glottal excitation.

18. The method of claim 16, wherein the time varying signal is processed to generate a sequence of first and second data values representing a characteristic of the signal.

19. The method of claim 18, wherein a first data value represents a first relative energy level associated with the time varying signal and a second data value represents a second relative energy level associated with the time varying signal.

20. The method of claim 8, wherein the comparing operation comprises correlating the first signal and the second signal to determine a relative fraction of matches between an unvoiced phone in the first signal and a relative low energy level portion of the second signal and between a voiced phone in the first signal and a relative high energy level portion of the second signal.

21. The method of claim 20, wherein the relative fraction of matches represents the level of correlation.

22. The method of claim 1, wherein the correlation level determining step is based on at least one of: a relative fraction of matches between the signals; mutual information between the signals; a measure of association between the signals; and a comparison of periodicities associated with the signals.

23. The method of claim 1, wherein the first signal is generated by an audio-based recognition system which includes at least one of a ballistic labeler, a speech recognition engine, and a classifier.

24. Apparatus for validating production of a biometric attribute allegedly associated with a user, the apparatus comprising:
   at least one processor operative to: (i) generate a first signal representing data associated with the biometric attribute allegedly received in association with the user; (ii) generate a second signal representing data associated with at least one feature detected in association with the production of the biometric attribute allegedly received from the user; and (iii) compare the first signal and the second signal to determine a correlation level between the biometric attribute and the production feature, wherein validation of the production of the biometric attribute depends on the correlation level; and
   memory, coupled to the at least one processor, for storing at least a portion of results associated with one or more operations performed in accordance with the at least one processor.

25. A system for validating production of a biometric attribute allegedly associated with a user, the system comprising:
   a biometric recognition device which generates a first signal representing data associated with the biometric attribute allegedly received in association with the user;
   a biometric production detecting device which generates a second signal representing data associated with at least one feature detected in association with the production of the biometric attribute allegedly received from the user; and
   a processor, operatively coupled to the biometric recognition device and the biometric production detecting device, which compares the first signal and the second signal to determine a correlation level between the biometric attribute and the production feature, wherein validation of the production of the biometric attribute depends on the correlation level.

26. The system of claim 25, wherein the biometric recognition device is a speech recognition device.

27. The system of claim 26, further comprising a speaker recognition device, coupled to the processor, for providing validation of the user.

28. The system of claim 27, wherein the speaker recognition device performs biometric recognition.

29. The system of claim 25, wherein the biometric recognition device is a speaker recognition device.

30. The system of claim 25, wherein the biometric attribute is a spoken utterance alleged to have been produced by the user and the system is integrated with one or more speech-based processing systems.

31. The system of claim 30, wherein the speech-based processing system is a biometric system.

* * * * *